United States Patent
Mitchell et al.

(10) Patent No.: US 7,893,940 B2
(45) Date of Patent: Feb. 22, 2011

(54) SUPER RESOLUTION CONTEXTUAL CLOSE-UP VISUALIZATION OF VOLUMETRIC DATA

(75) Inventors: Ross Mitchell, Calgary (CA); Sonny Chan, Calgary (CA); Mario Costa Sousa, Calgary (CA); Torin Taerum, Calgary (CA); Faramarz Samavati, Calgary (CA)

(73) Assignee: Calgary Scientific Inc., Calgary, Alberta (CA)

( * ) Notice: Subject to any disclaimer, the term of this patent is extended or adjusted under 35 U.S.C. 154(b) by 998 days.

(21) Appl. No.: 11/729,834

(22) Filed: Mar. 30, 2007

(65) Prior Publication Data

US 2008/0055310 A1 Mar. 6, 2008

Related U.S. Application Data

(60) Provisional application No. 60/787,699, filed on Mar. 31, 2006.

(51) Int. Cl.
*G06T 17/00* (2006.01)
(52) U.S. Cl. .................. 345/424; 345/419; 345/420
(58) Field of Classification Search .......... 345/419–428
See application file for complete search history.

(56) References Cited

U.S. PATENT DOCUMENTS

| | | | |
|---|---|---|---|
| 7,015,906 B2 | 3/2006 | Olschewski et al. | |
| 7,280,105 B2* | 10/2007 | Cowperthwaite | 345/419 |
| 7,633,501 B2* | 12/2009 | Wood et al. | 345/419 |
| 2003/0128890 A1 | 7/2003 | Roesch et al. | |
| 2004/0125103 A1 | 7/2004 | Kaufman et al. | |
| 2007/0024639 A1 | 2/2007 | Hastings | |

FOREIGN PATENT DOCUMENTS

| | | |
|---|---|---|
| EP | 1 012 812 B1 | 11/2004 |
| WO | 02/056240 A1 | 7/2002 |

OTHER PUBLICATIONS

Bruckner et al., Volumeshop: An Interactive System for Direct Volume Illustration, Proceedings of IEEE Visualization 2005, Oct. 2005.*
Bier et al., Toolglass and Magic Lenses: The See-Through Interface, Proceedings of SIGGRAPH '93, 1999, pp. 73-80.*
Csebfalvi et al., Fast Visualization of Object Contours by Non-Photorealistic Volume Rendering, Eurographics Vol. 20, No. 3, 2001.*

(Continued)

*Primary Examiner*—Xiao M Wu
*Assistant Examiner*—Charles Tseng
(74) *Attorney, Agent, or Firm*—Freedman & Associates (57) ABSTRACT

The present invention relates to a method and system for processing a volumetric dataset for providing close-up visualization of a subset therefrom. A volumetric dataset is processed based on a dual access gradient quantization data structure. The data structure is generated in a fast pre-processing stage and provides substantially immediate access to a quantized gradient using either an index or an arbitrary normalized vector. The method provides a clear, enlarged high-resolution image of a user selected region of interest at interactive rates and allows the user to freely move and visualize the region of interest within the volumetric dataset and with any orientation.

29 Claims, 9 Drawing Sheets

OTHER PUBLICATIONS

Meißner et al., *"Volume Visualization and Volume Rendering Techniques"*, In: Tutorials 6, Eurographics 2000, Interlaken, Switzerland, pp. 1 to 36 [Retrieved on May 24, 2007]. (Retrieved from the Internet at URL:http://www.gris.uni-tuebingen.de/people/staff/meissner/tutorials/tutorial.pdf) pp. 1 to 31.

Piccand et al., *"Efficient Visualization of Volume Data Sets with Region of Interest and Wavelets"*, SPIE 2005, pp. 1 to 9 [Retrieved on May 24, 2007]. Retrieved from the Internet at URL:http://profs.logti.etsmtl.ca/paquette/Research/Papers/Paquette.2005.MI/Piccand.2005.spie.mi.pdf) pp. 1 to 3.

Balázs. *"Interactive Volume-Rendering Techniques for Medical Data Visualization"*, Dissertation, Institut für Technische Naturwissenschaften and Informatik, May 2001, pp. 1 to 83 [Retrieved on May 24, 2007]. (Retrieved from the Internet at URL:http://www.cg.tuwien.ac.at/research/publications/2001/Csebfalvi-thesis/Csebfalvi-thesis-PDF.pdf) pp. 9 to 44, 73 and 74.

Sato et al., *"A Viewpoint Determination System for Stenosis Diagnosis and Quantification in Coronary Angiographic Image Acquisition"*, IEEE Transactions on Medical Imaging, Vol. 17, No. 1, Feb. 1998, pp. 121-137.

* cited by examiner

SUPER RESOLUTION CONTEXTUAL CLOSE-UP VISUALIZATION OF VOLUMETRIC DATA

FIELD OF THE INVENTION

This invention relates to visualization of volumetric data and in particular to a data processing method and system for super resolution contextual close-up visualization of volumetric data.

BACKGROUND OF THE INVENTION

Given current advances in imaging devices and computer processing power, volumetric datasets are produced in numerous different applications. For example, more and more present-day imaging systems such as Magnetic Resonance Imagers (MRI) or Computed Tomography (CT) produce volumetric datasets providing a clinical practitioner with substantially more information by allowing viewing of an imaged region of a patient's body from various viewing directions. Furthermore, various fields such as meteorology, geophysics, astrophysics, and engineering benefit these days from measurements and computer simulations producing volumetric datasets.

However, visualization of the volumetric datasets presents specific challenges not found in representations of two dimensional data. In 2D representations all information is restricted to a plane perpendicular to a view point. The addition of the third dimension allows objects to be interposed between the view point and other objects in a scene. Therefore, the preservation of spatial relationships is important in constructing a physically plausible scene or, in other words, the detail of the scene needs to be maintained in the context in which it exists.

Increasing availability of powerful workstations has fueled the development of new methods for visualizing a volumetric dataset—commonly represented by a 3D grid of volume elements or voxels. The process of presenting a volumetric dataset from a given viewpoint is commonly referred to as volume rendering, and is one of the most common techniques for visualizing a 3D object or phenomenon represented by voxels at the grid points of the volumetric dataset.

Various applications often require effective and fast visualization of internal features of a volumetric dataset. In a clinical application, for instance, rapid determination of size, shape, and spatial location of a lesion can be life-saving in emergency situations. To this end, clinicians need to have quick close-up visualization of the data from multiple viewing directions in high-quality images of a specific internal Region Of Interest (ROI), while preserving overall contextual and spatial information.

Present multi-resolution techniques for volume rendering are based on a brick data structure to allow various levels of detail, as disclosed, for example, in LaMar E., Hamann B., Joy K.: "*Multiresolution techniques for interactive texture-based volume visualization*", Proc. IEEE Visualization '99 (1999), pp. 355-543; in Weiler M., Westermann R., Hansen C., Zimmermann K., Ertl T.: "*Level-of detail volume rendering via 3D textures*", Proc. IEEE Volume Visualization and Graphic Symposium '00 (2000); and in Wang C., Shen H.-W.: "*Hierarchical navigation interface: Leveraging multiple coordinated views for level-of-detail multiresolution volume rendering of large scientific datasets*", Proc. of International Conference on Information Visualization '05 (2005). Unfortunately, these techniques require processing of large data volumes during user interactivity, for example, for selecting a ROI or changing a viewing direction, resulting in a slow response of the processing system and, consequently, making the viewing of a large volumetric dataset an arduous task.

Existing techniques for direct volume rendering also suffer from the problem of occlusion by exterior 1features. Transfer functions, clipping, or segmentation have been applied to alleviate this problem, as disclosed, for example, in Bruckner S., Grimm S., Kanitsar A., Gröller M. E.: "*Illustrative context-preserving volume rendering*", Proc. of EuroVis 2005 (2005), pp. 69-76. However, these techniques typically obscure details in the final image with overlapping structures and remove important contextual information.

It would be highly desirable to overcome the drawbacks of the present techniques by providing fast high resolution close-up visualization of a ROI for use with off-the-shelf Graphics Processing Units (GPU) on a personal computer or workstation. It would be further highly beneficial to provide a contextual close-up visualization of a ROI without obscuring details.

SUMMARY OF THE INVENTION

It is, therefore, an object of the invention to provide a data processing method and system for providing fast super resolution close-up visualization of a ROI of a volumetric dataset.

It is further an object of the invention to provide fast super resolution close-up visualization of a ROI of a volumetric dataset for use with off-the-shelf Graphics Processing Units (GPU) on a personal computer or workstation.

It is yet further an object of the invention to provide a contextual close-up visualization of a ROI of a volumetric dataset without obscuring details.

In accordance with the present invention there is provided a method for processing a volumetric dataset for providing close-up visualization of a subset therefrom comprising:

receiving the volumetric dataset, the volumetric dataset being indicative of one of an object and a physical event;

determining a quantized gradient vector for each voxel of the volumetric dataset;

generating a gradient table comprising the quantized gradient vectors of the volumetric dataset;

generating a secondary gradient table comprising indices pointing to respective entries in the gradient table;

generating a 3D array index table, the 3D array index table comprising an index into the gradient table for each voxel of the volumetric dataset;

receiving first subset data indicative of a first subset;

subdividing the first subset;

determining a quantized new gradient vector for each new voxel of the subdivided first subset;

using the secondary gradient table determining for each new quantized gradient vector a closest quantized gradient vector of the gradient table and its index;

generating a 3D array subset index table, the 3D array subset index table comprising an index into the gradient table for each voxel of the subdivided first subset;

using the 3D array index table and the 3D array subset index table, rendering the volumetric dataset and the subdivided first subset, respectively; and, graphically displaying the rendered volumetric dataset and the rendered subdivided first subset.

In accordance with an aspect of the present invention there is provided a method for providing contextual close-up visualization comprising:

receiving a volumetric dataset, the volumetric dataset being indicative of one of an object and a physical event;

receiving data indicative of a volumetric subset of the volumetric dataset;

rendering the volumetric dataset and the volumetric subset in dependence upon a first viewing direction;

using a graphical display, simultaneously displaying the rendered volumetric dataset and the rendered volumetric subset, wherein the rendered volumetric subset is displayed in a predetermined close-up area on the graphical display;

providing a visual cue connecting the close-up area with a location of the volumetric subset within the volumetric dataset; and, rendering the volumetric subset in dependence upon a second viewing direction and simultaneously displaying the rendered volumetric dataset and the subset rendered in dependence upon the second viewing direction being displayed in the close-up area.

In accordance with the present invention there is further provided a storage medium having stored therein executable commands for execution on a processor, the processor when executing the commands performing processing a volumetric dataset for providing close-up visualization of a subset therefrom comprising:

receiving the volumetric dataset, the volumetric dataset being indicative of one of an object and a physical event;

determining a quantized gradient vector for each voxel of the volumetric dataset;

generating a gradient table comprising the quantized gradient vectors of the volumetric dataset;

generating a secondary gradient table comprising indices pointing to respective entries in the gradient table;

generating a 3D array index table, the 3D array index table comprising an index into the gradient table for each voxel of the volumetric dataset;

receiving first subset data indicative of a first subset;

subdividing the first subset;

determining a quantized new gradient vector for each new voxel of the subdivided first subset;

using the secondary gradient table determining for each new quantized gradient vector a closest quantized gradient vector of the gradient table and its index;

generating a 3D array subset index table, the 3D array subset index table comprising an index into the gradient table for each voxel of the subdivided first subset;

using the 3D array index table and the 3D array subset index table, rendering the volumetric dataset and the subdivided first subset, respectively; and, graphically displaying the rendered volumetric dataset and the rendered subdivided first subset.

In accordance with the aspect of the present invention there is further provided a storage medium having stored therein executable commands for execution on a processor, the processor when executing the commands performing:

receiving a volumetric dataset, the volumetric dataset being indicative of one of an object and a physical event;

receiving data indicative of a volumetric subset of the volumetric dataset;

rendering the volumetric dataset and the volumetric subset in dependence upon a first viewing direction;

using a graphical display, simultaneously displaying the rendered volumetric dataset and the rendered volumetric subset, wherein the rendered volumetric subset is displayed in a predetermined close-up area on the graphical display;

providing a visual cue connecting the close-up area with a location of the volumetric subset within the volumetric dataset; and, rendering the volumetric subset in dependence upon a second viewing direction and simultaneously displaying the rendered volumetric dataset and the subset rendered in dependence upon the second viewing direction being displayed in the close-up area.

In accordance with the present invention there is yet further provided a system for processing a volumetric dataset for providing close-up visualization of a subset therefrom comprising:

a first input port for receiving the volumetric dataset, the volumetric dataset being indicative of one of an object and a physical event;

a processor in communication with the first and the second input port for processing the volumetric dataset comprising:

determining a quantized gradient vector for each voxel of the volumetric dataset;

generating a gradient table comprising the quantized gradient vectors of the volumetric dataset;

generating a secondary gradient table comprising indices pointing to respective entries in the gradient table;

generating a 3D array index table, the 3D array index table comprising an index into the gradient table for each voxel of the volumetric dataset;

receiving subset data indicative of a subset;

subdividing the subset;

determining a quantized new gradient vector for each new voxel of the subdivided subset;

using the secondary gradient table determining for each new quantized gradient vector a closest quantized gradient vector of the gradient table and its index;

generating a 3D array subset index table, the 3D array subset index table comprising an index into the gradient table for each voxel of the subdivided subset; and, using the 3D array index table and the 3D array subset index table, rendering the volumetric dataset and the subdivided subset, respectively, and providing data in dependence thereupon; and, an output port in communication with the processor for providing the data indicative of the rendered volumetric dataset and the rendered subdivided subset.

BRIEF DESCRIPTION OF THE FIGURES

Exemplary embodiments of the invention will now be described in conjunction with the following drawings, in which.

DETAILED DESCRIPTION OF THE INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein.

Figure 1:
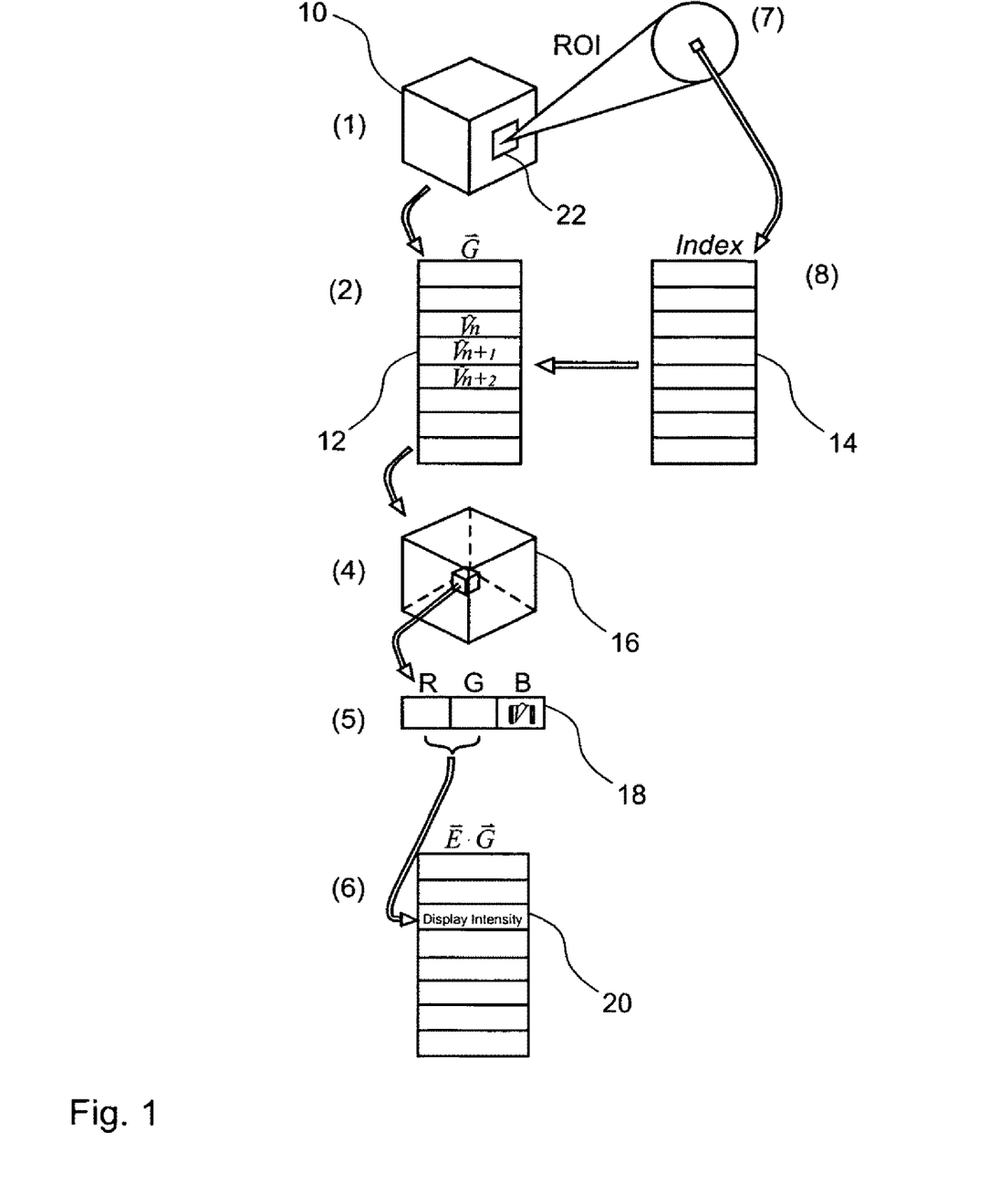
FIG. 1 is a simplified diagram illustrating key steps of a method for processing a volumetric dataset for providing close-up visualization of a subset therefrom according to the invention.

Referring to FIG. 1, a simplified diagram illustrating seven key steps of a method for providing super resolution contextual close-up visualization of a volumetric subset—ROI 22—of a volumetric dataset 10 according to the present invention is shown. In order to provide a better understanding, an overview of the key steps will be given first, with reference to FIG. 1, followed by a detailed description of the various components thereafter. The seven key steps are as follows:

(1) The volumetric dataset 10 is loaded, for example, into a CPU of a personal computer, and preprocessed for producing a decimated copy of the dataset 10 for fast interaction therewith, preferably, using B-spline multi-resolution reverse subdivision. Further, a gradient vector ∇ is calculated and quantized for each voxel of the dataset 10. Employment of an optimized quantization process ensures fast quantization.

(2) The quantized gradients ∇ of the dataset 10 are stored in a, typically short, "static" primary lookup table—gradient table 12. Indices into this table are used to construct a quantized gradient volume in steps (4) and (5) below.

(3) A secondary gradient table—index table 14 is constructed with indices pointing to entries in the gradient table 12. The index table 14 is used to access an existing quantized gradient ∇ in the gradient table 12 in dependence upon an arbitrary new gradient vector of the ROI 22 determined in step (7) below.

(4) An index into the gradient table 12 for each data voxel is stored in a 3D array index table 16. This 3D array has same dimensions as the volumetric dataset 10. Preferably, the 3D array index table 16 is uploaded to a GPU of the personal computer and stored as a 3D array. This allows fast access to gradient information on a per-voxel basis within a GPU program.

(5) Gradient information of each 3D array element is stored as an RGB value 18. The R and G components hold the index into the gradient table 12. This index is used to access a "display intensity table" 20, see step (6) below. The B component contains the magnitude of the quantized gradient for a corresponding data voxel. The gradient magnitude is used for transfer functions, for example, for Phong shading.

(6) The display intensity table 20 is a list of greyscale values. The display intensity table 20 has a same length as the gradient table 12, above. Thus, it is possible to use the same set of indices to index into either table. Table elements are determined by calculating an inner product between a current view—or lighting—vector E and the quantized gradient vector G from step (2). The display intensity table 20 is updated each time the view is changed. However, since the quantized primary gradient table 12 is short, this operation is fast—typically less than 1 ms.

(7) During execution, contextual close-up views are created. A subset of the dataset 10 corresponding to a ROI 22 selected by a user is determined inside the dataset 10. B-spline subdivision of the subset yields a super-resolution subset that is rendered enlarged and separated from the subset. For example, a $128^3$ super-resolution subset is obtained from a $64^3$ subset. The index table 14 determined in step (3) enables fast gradient dependent rendering of the subset 22.

Volumetric datasets are generally very large. For example, a volumetric dataset of a 3D CT scan comprises 512×512× 256 voxels, with 16 bit samples for each voxel. Although state of the art graphics devices are now equipped with enough memory to store such a volumetric dataset most devices are not capable of rendering such a full resolution volume at interactive rates, i.e. without a substantial delay between a user request and a graphical response thereupon.

In order to ensure that the volumetric dataset 10 is viewed and manipulated at interactive rates, while still allowing full resolution viewing and detailed high resolution exploration, the volumetric dataset 10 is represented using a B-spline tensor at multiple resolutions. For representing a selected ROI 22 it is necessary to determine a higher resolution image from the volumetric data using an interpolation process. Tri-linear interpolation is commonly used in computer graphics hardware, however, the resulting image quality is not sufficient for most applications. B-spline functions provide superior image quality compared to linear interpolations. Rather than evaluating the B-spline basis functions, a B-spline subdivision process is used since it is substantially faster and enables an efficient hierarchical multi-resolution structure.

The full B-spline representation of a trivariate dataset is as follows:

$$L(u, v, w) = \sum_{i=0}^{p-1} \sum_{j=0}^{q-1} \sum_{k=0}^{r-1} V_{ijk} B, \tag{1}$$

where $V_{ijk}$ are intensities from an image with dimensions p×q×r, and $B=B_i^m(u)B_j^m(v)B_k^m(w)$ are the basis functions for the B-spline, with m being the order of the B-spline. Since functional evaluation of equation (1) is not fast enough for provision of high resolution images at interactive rates, a subdivision process is applied for fast evaluation of equation (1). For example, a Chaikin subdivision process is capable of generating sufficiently fast a quadratic B-spline:

$$c_{2i}^{k+1} = \frac{1}{4} c_{i-1}^k + \frac{3}{4} c_i^k c_{2i-1}^{k+1} = \frac{3}{4} c_i^k + \frac{1}{4} c_{i+1}^k, \tag{2}$$

where k and k+1 refer to the lower and higher resolution datasets, respectively, and $C_{i-1}, C_i, C_{i+1}$ denote three consecutive voxel values along one of the main directions of the dataset. Independent application of this process over all three main directions of the trivariate dataset provides a super-resolution representation of the selected ROI 22. Of course, it is also possible to generate higher order B-splines.

To provide "real-time" graphical user interaction, for example, for selecting a viewing direction or a ROI 22, a low resolution approximation of the volumetric dataset 10 is used. To this end, a reverse Chaikin process is applied:

$$c_i^k = -\frac{1}{4}c_{2i-1}^{k+1} + \frac{3}{4}C_{2i}^{k+1} + \frac{3}{4}c_{2i+1}^{k+1} - \frac{1}{4}c_{2i+2}^{k+1}, \quad (3)$$

where k+1 refers to the normal resolution dataset and k to the low resolution approximation. Independent application of this process over all three main directions of the volumetric dataset provides a 3D low resolution approximation of the volumetric dataset. As is evident, other interpolation processes are also applicable for obtaining the low resolution approximation. However, the reverse Chaikin process is preferred to provide a consistent framework with the B-spline process used for the super-resolution process.

For example, for a volumetric dataset of size $N^3$, equation (3) is applied in all three main directions to obtain a low resolution approximation of size $$\left(\frac{N}{2}\right)^3.$$

Figure 2A:
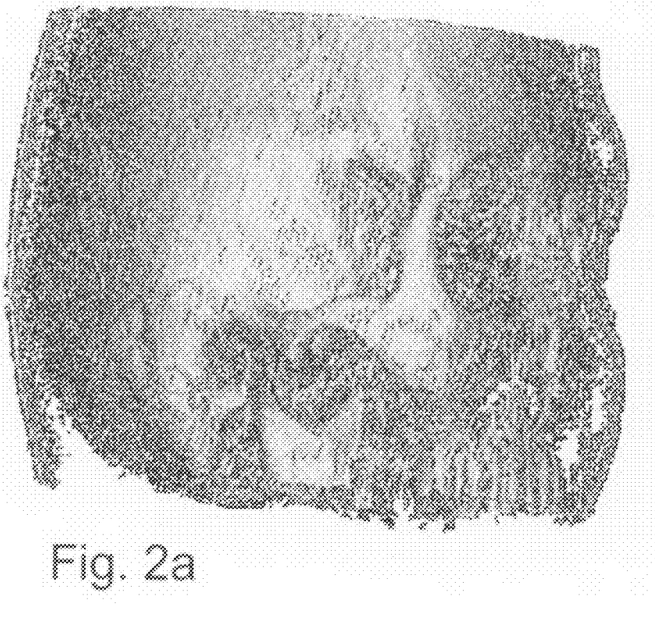
FIGS. 2a and 2b are diagrams illustrating a CT volume rendered with a silhouette with the diagram in FIG. 2a being a low-resolution approximation during user interaction and FIG. 2b being normal resolution after interaction.
Figure 2B:
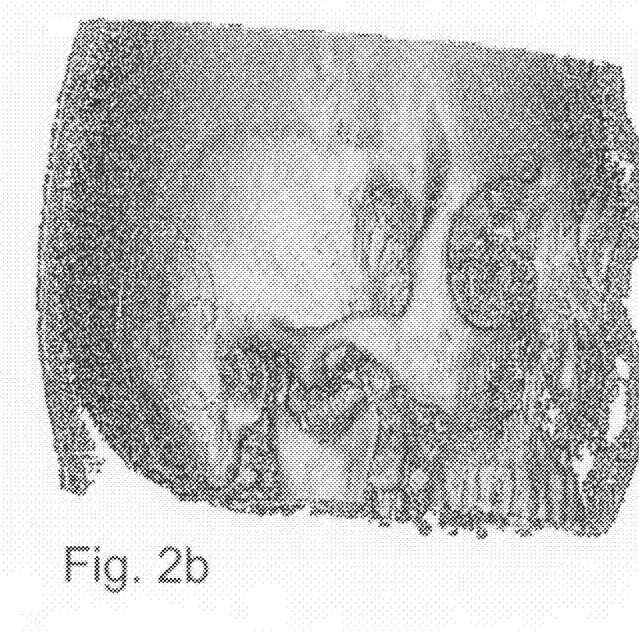

As is evident, computer graphics hardware is capable of rendering the low resolution approximation substantially faster than the original volumetric dataset. Therefore, the low resolution approximation is rendered anytime the user interacting with the graphical computer system, shown in FIG. 2a, and upon cessation of the interaction the system returns to the original resolution, shown in FIG. 2b. For, example, the low resolution approximation is determined at a first user interaction and then stored in memory ensuring fast transition.

Figures 3A, 3B:
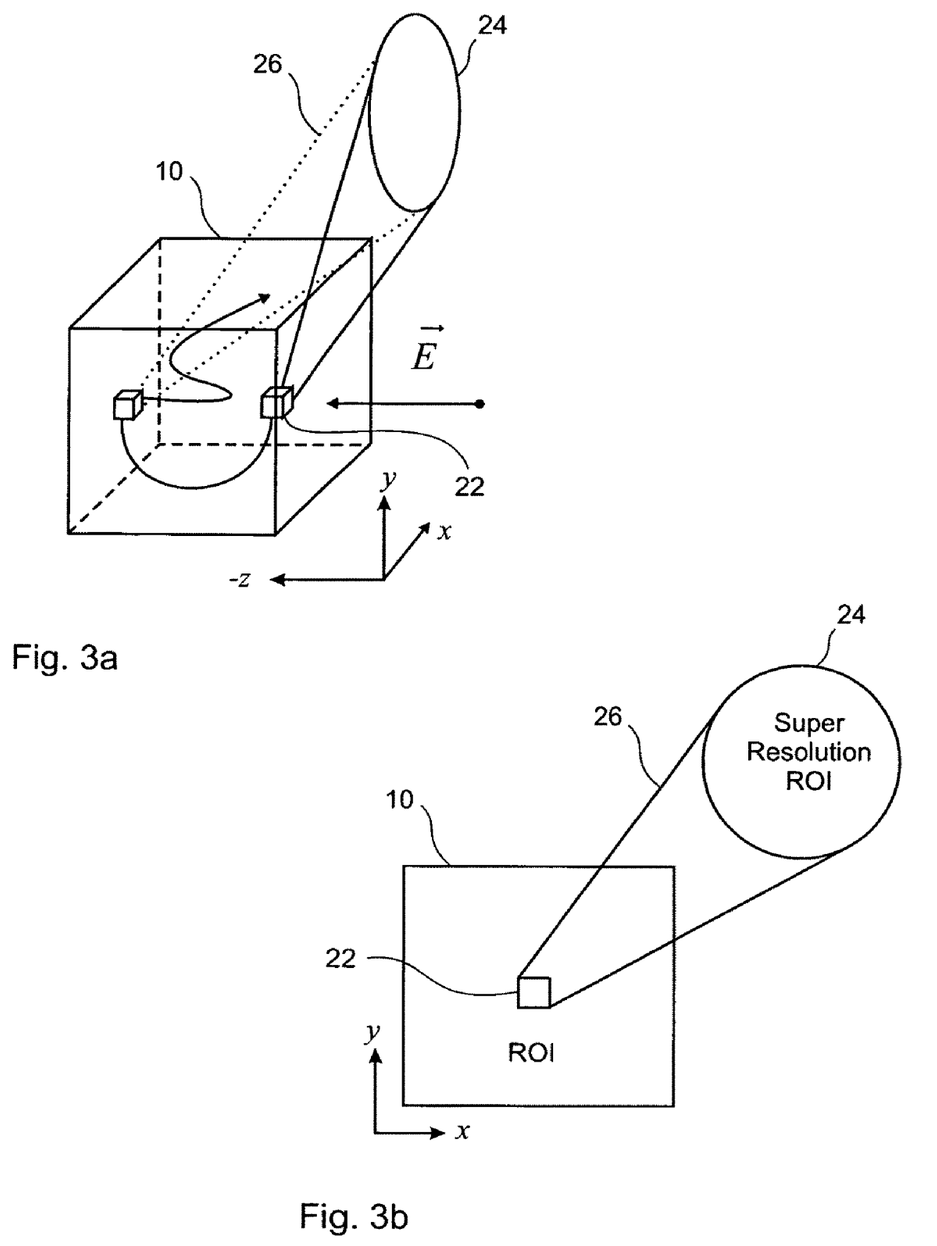
FIGS. 3a to 3d are simplified block diagrams illustrating a ROI within a volumetric dataset and its representation.
Figure 3C:
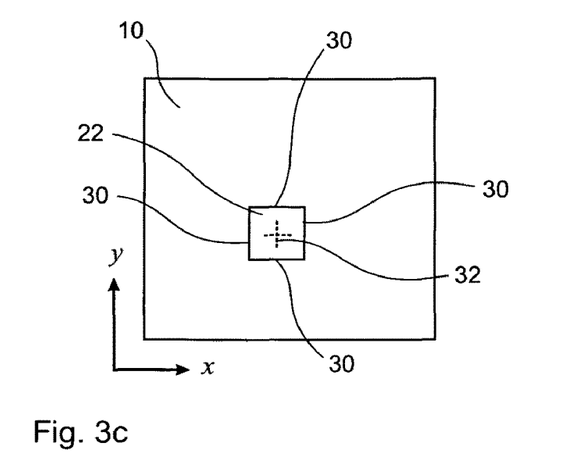
Figure 3D:
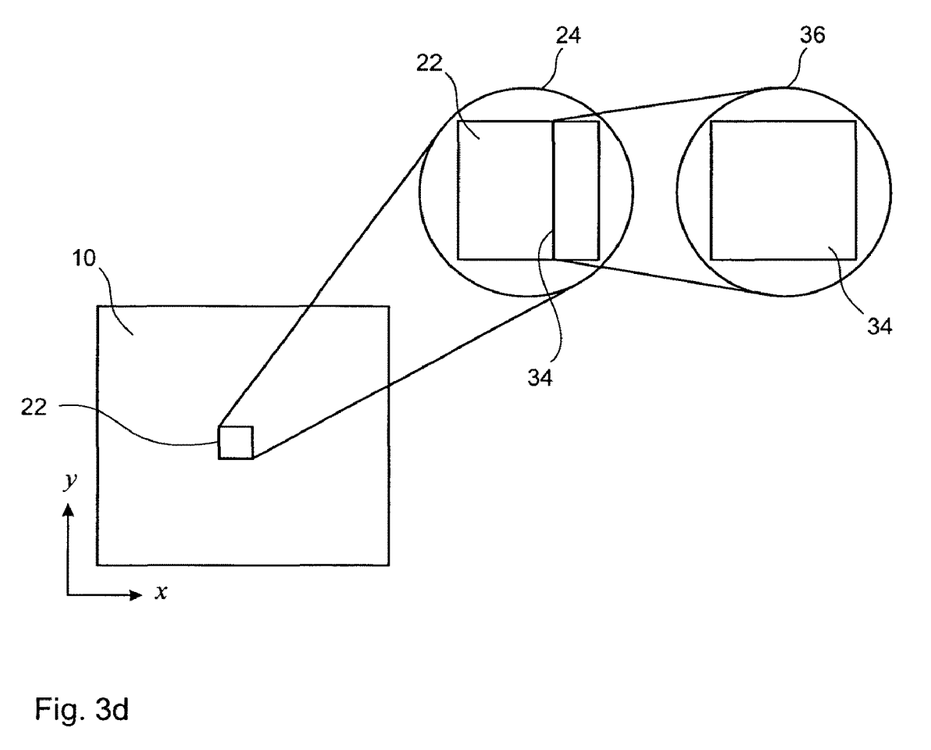

Referring to FIGS. 3a and 3b, a contextual close-up visualization of a ROI 22 of a volumetric dataset 10 according to the invention is shown. FIG. 3a shows a ROI 22 represented as a sub-volume of the volumetric dataset 10. Based on a current viewing direction E an image of the original volume 10 and, in close-up area 24, a close-up super-resolution image of the ROI 22 is shown in. FIG. 3b illustrates a two dimensional image—comprising an image of the original volume 10 and a close-up of the ROI 22—based on the viewing direction E as shown, for example, on a computer screen. In order to realize the close-up visualization, a 3D position inside the volumetric dataset 10 is stored as the center of the ROI 22. An initial size, defining for example a box-shaped sub-volume, for the ROI 22 is also stored. The user is then free to move the ROI 22 to any position within the volume 10 and, optionally, change the size of the ROI 22. As the ROI 22 is moved, the sub-volume defined by the position of the ROI 22 as well as its size is updated. Additionally, the user is enabled to rotate the ROI in order to explore an internal feature from different viewing directions. Preferably, the image of the volume 10 is rendered with the ROI 22 fully exposed. This is achieved with a shape in the stencil buffer. The close-up image based on the super-resolution ROI 22 is rendered enlarged in the close-up area 24—for example, a circular or rectangular window—placed in a different area on the computer screen. Then a translucent cone 26, connecting the ROI 22 inside the volume 10 with the close-up image in the close-up area 24, is rendered. This results in the ROI 22 being visible both at its physical location within the original volume 10 and in a separated screen area drawing attention to it. The close-up image of the ROI 22 is typically not occluded since its texture consists only of the sub-volume defined by its position and size. However, context is still available since the image of the original volume is rendered in full. The translucent cone 26 provides a visual cue that connects the close-up image of the ROI 22 to the location where it exists spatially inside the original volume 10. Optionally, in the view of the volume 10 the ROI 22 is indicated, for example, by using at least one of lines 30 indicating a boundary of the ROI 22 and "cross hairs" 32 indicating the center of the ROI 22, as shown in FIG. 3c. The indicators 30 and 32 are updated in the 2D view of the volume 10 with movement of the ROI 22 within the volume 10. Further optionally, a user is enabled to use the indicators 30 and 32 in the 2D view of the volume 10 for selecting the ROI 22 and to move the same within the volume 10. Since the user is able to move the ROI 22 to any position within the volume 10, it is helpful to provide some form of depth cueing. For example, changing luminance of the translucent cone 26 helps the user to perceive the depth of the ROI 22 within the volume 22. Further optionally, the user is enabled to simultaneously change the viewing direction of the volume 10 and the ROI 22. Further optionally, the user is enabled to change size and position of the close-up area 24 on the computer screen.

Furthermore, it is possible to use different rendering techniques for rendering the volume 10 and the ROI 22 as well as to provide a user with additional examination tools for examining the ROI 22 visualized in the close-up area 24. For example, the user is enabled to select planes 34 within the ROI 22 for visualizing the same in a second close-up area 36, as shown in FIG. 3c. The planes 34 are, for example, 3 orthogonal planes fixed within the ROI 22 or movable along orthogonal coordinates of the ROI 22. Alternatively, the user is enabled to determine location and orientation of the planes within the ROI 22 in an arbitrary fashion. Optionally, the user is enabled to determine a plurality of planes which are user selectable displayed in a single second close-up area 36 or, alternatively, displayed simultaneously in a plurality of second close-up areas 36. With changes of the ROI 22—for example, movement, viewing direction, rendering technique—visualization of the planes 34 is changed accordingly.

Figure 4A:
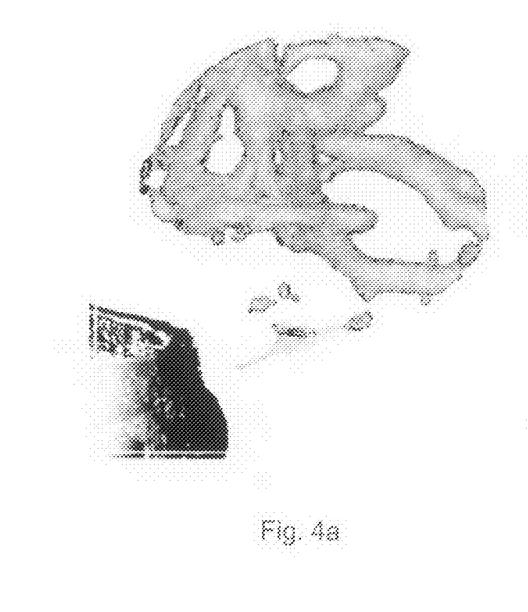
FIGS. 4a to 4c are diagrams illustrating different levels of smoothness in dependence upon the subdivision of the ROI.
Figure 4B:
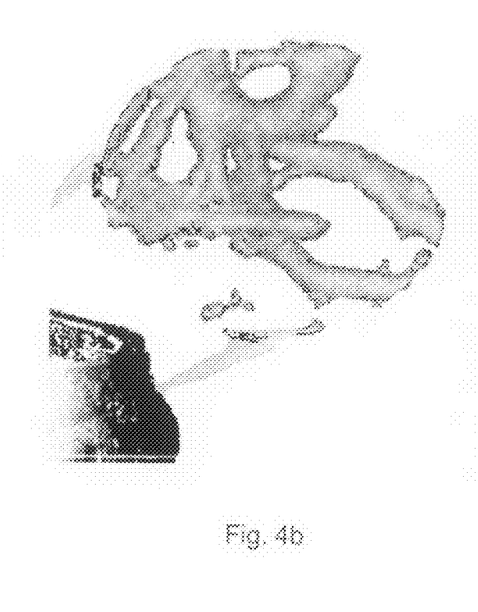
Figure 4C:
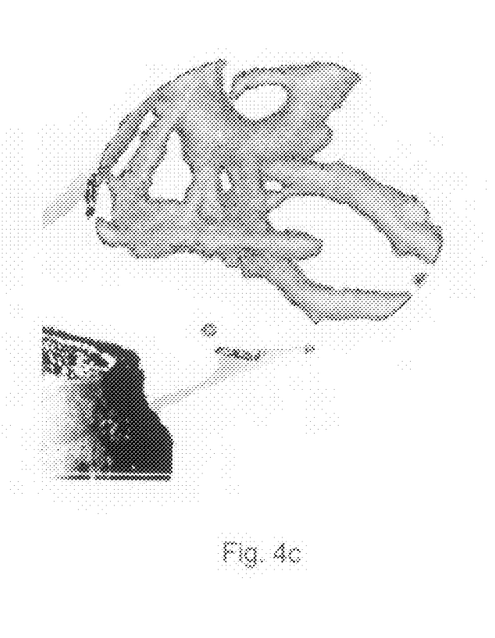

As discussed above, since the ROI 22 sub-volume is rendered enlarged B-spline subdivision is applied to the data of the sub-volume to create a smooth super-resolution representation of the ROI 22. The user is provided with the option to choose the order of the B-spline to allow for different levels of smoothness, as illustrated in the example of FIGS. 4a to 4c, with: FIG. 4a being generated without B-spline subdivision; FIG. 4b being generated using $3^{rd}$ order B-spline subdivision; and FIG. 4c being generated using $4^{th}$ order B-spline subdivision.

When the ROI 22 has the B-spline subdivision applied, in order to still have gradient dependent rendering techniques available, a process for quickly determining finer gradients in the ROI 22 is needed. One option is to simply evaluate the gradients via central differences. However, this process requires a square root operation for normalizing the gradient vector. A substantially faster process is to apply the same B-spline subdivision used for the scalar image values to the existing, already normalized gradients. Because the B-spline subdivision has the property of unit summation, the gradient vectors resulting from the subdivision are already normalized.

Gradient dependent rendering techniques are important for direct illustrative volume rendering. Two techniques of primary concern are silhouette enhancement and shading. Extraction and rendering of a silhouette is a valuable feature of an image of a volumetric dataset, especially when dealing with internal features. Since volumetric datasets are very large, attempting to visualize the entire volume at once is visually overwhelming. Silhouettes provide a trade-off that is ideal for volume rendering since it depicts the most information, i.e. important shape features, while rendering the least.

to the gradient table 12—line 8—if the value res has not been encountered yet—line 6. The position at which $\nabla$ is added, is stored in the index table 14 at res—line 9 and FIG. 5a. The index for the quantized gradient—whether newly inserted or not—is then returned. There is a trade-off between image quality and processing speed, which is determined by the user choosing a value for the scale factor $\gamma$. Table 1 illustrates the results for various values of $\gamma$.

TABLE 1

| Scale ($\gamma$) | Gradient Table Size | Index Table Size | Mean Error | Maximum Error | Access Time [ms] |
|---|---|---|---|---|---|
| 4-7 | 314-938 | 4096 | 8.95e−3-3.14e−3 | 6.15e−2-2.38e−2 | 125 |
| 8-15 | 1250-4249 | 32768 | 2.54e−3-7.33e−4 | 1.86e−2-5.48e−3 | 125 |
| 16-31 | 4874-17974 | 262144 | 6.29e−4-1.63e−4 | 5.09e−3-1.39e−3 | 125-172 |
| 32-63 | 19128-72381 | 2097152 | 1.55e−4-3.89e−5 | 1.28e−3-3.38e−4 | 281-407 |
| 64-127 | 75060-284599 | 16777216 | 3.73e−5-9.57e−6 | 3.37e−4-8.18e−5 | 468-562 |
| 128-255 | 289284-1072340 | 134217728 | 9.45e−6-2.34e−6 | 8.39e−5-2.05e−5 | 640-797 |

In a volume, a voxel v is labeled a "silhouette voxel" if $\vec{E} \cdot \vec{G}) = 0$, where $\vec{E}$ is the view vector, and $\vec{G}$ is a voxel intensity gradient. Shading with direct volume rendering implies having the luminance of a voxel determined using a shading model calculation. It is important that it provides the user with a basic indication of shape. The shading requires the calculation of ($\vec{L} \cdot \vec{G}$), where $\vec{L}$ is a light vector for a directional light source.

Figure 5A:
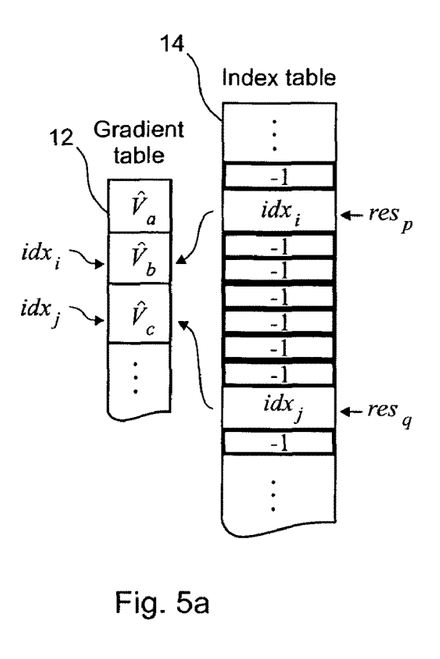
FIGS. 5a and 5b are simplified diagrams illustrating a dual access gradient quantization data structure according to the invention for use in the method shown in FIG. 1.
Figure 5B:
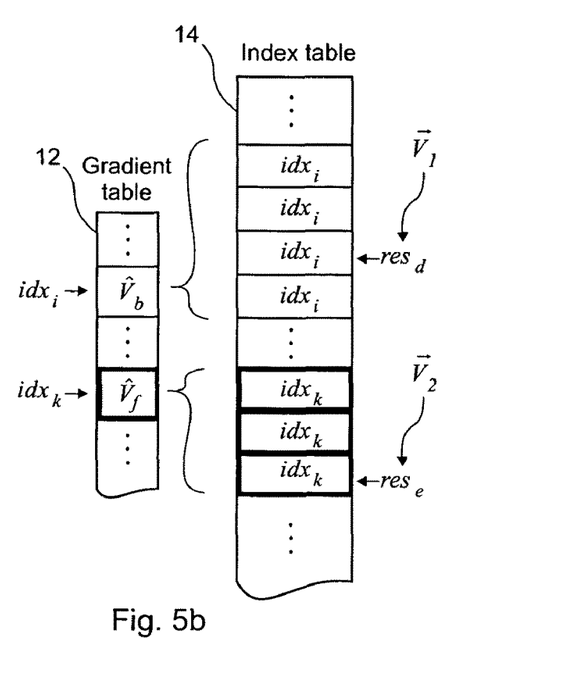

A primary issue of the volumetric gradient dependent rendering is the evaluation of the inner products between the gradient and other directions, i.e. viewing and lighting, which is substantially facilitated by using gradient quantization techniques. For use with the method shown in FIG. 1 a dual access gradient quantization has been designed as will be described in the following. For this process two lookup tables, shown in FIGS. 5a and 5b, are generated: a gradient table 12—an array of quantized gradient vectors $\hat{V}$—and an index table 14—an array of integers, whose elements are an entry to the gradient table 12. The index table 14 is used to access a quantized gradient with an arbitrary vector, as shown in FIG. 5b with vectors $\vec{V}_1$ and $\vec{V}_2$. To generate the two lookup tables as the gradient of each voxel is calculated and normalized, a quantization function is applied to the voxel intensity gradient, as described by the following process:

| | Quantize Gradient |
|---|---|
| 1 | $\vec{V} \cdot (x, y, z) \leftarrow$ round($\hat{G} \cdot (x, y, z) \times \gamma$) |
| 2 | rx $\leftarrow (\vec{V} \cdot x + \gamma) << (b \times 2)$ |
| 3 | ry $\leftarrow (\vec{V} \cdot y + \gamma) << (b)$ |
| 4 | rz $\leftarrow (\vec{V} \cdot z + \gamma)$ |
| 5 | res $\leftarrow$ (rx + ry + rz) |
| 6 | if index [res] = −1 |
| 7 | then idx $\leftarrow$ next entry in gradient table |
| 8 | gradient [idx] $\leftarrow \vec{V}$ |
| 9 | index [res] $\leftarrow$ idx |
| 10 | return idx |
| 11 | return index [res] |

In the Quantize Gradient process, $\hat{G}$ is the incoming gradient vector, $\gamma$ is a small integer scale factor chosen at compilation time and b is a number of minimum bits needed to represent ($\gamma \times 2$)+1. The incoming gradient vector $\hat{G}$ has components x, y, and z in the range [−1.0, 1.0]. After line 1, the vector $\vec{V}$ has components x, y, and z in the range [−$\gamma$, $\gamma$]. Line 5 results in res$\in [0, 2^{3b}]$. The new vector $\vec{V}$ is only normalized and added The error values have been determined as cos($\theta$) between an incoming gradient vector and the vector returned from the quantized gradient table 12. The access times have been determined for performing 2 million lookups using a vector, which is equivalent to a typical size of the ROI 22. In experiments it has been observed that a value of 31 for $\gamma$ results in fast access and a reasonably small size of the gradient table 12. This ensures that a sufficient small number of inner products are determined for gradient dependent rendering. Additionally, only 2 bytes are needed for each of the indices.

Figure 6:
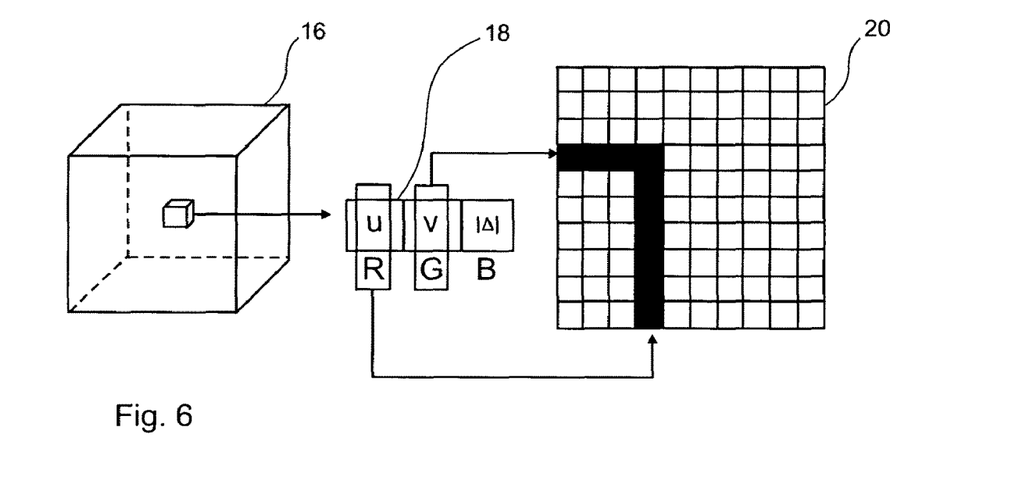
FIG. 6 is a simplified diagram illustrating a 3D array index table structure according to the invention for use in the method shown in FIG. 1.

For each voxel the index returned by the Quantize Gradient process is stored in a 3D array 16 using RGB format 18, as shown in FIG. 6. The silhouette or shading intensity is indexed via an array indirection. With a view change only the small 2D intensity array 36 is updated. The gradient magnitude |$\Delta$| is used for other transfer functions. Since the index requires 2 bytes for $\gamma$=31, it is stored such that the R component contains the high order byte and the G component contains the low order byte.

Once each voxel gradient has been quantized, the result is a relatively small table of unique quantized gradients 12, FIG. 5a, and a slightly larger, however not full, table of indices 14 pointing to entries in the gradient table 12, FIG. 5b. Additionally, each voxel contains a 2 byte index into the gradient table 12, FIG. 6.

The quantized gradient table 12 is used for fast gradient depending rendering. Each time the view changes a scalar intensity is calculated using the quantized gradient table 12. For the silhouette extraction and enhancement the following equation is used:

$$I_{silhouette} = 1 - abs(\vec{E} \cdot \vec{G})^\alpha \qquad (4)$$

where $\vec{E}$ and $\vec{G}$ denote the view and the gradient vectors, respectively, and $\alpha$ indicates the sharpness of the silhouette. For Phong shading, a directional light source is placed at the eye, i.e. $\vec{L} = \vec{E}$ resulting in the following equation:

$$I_{phong} = abs(\vec{E} \cdot \vec{G}) + abs(\vec{R} \cdot \vec{G})^n \qquad (5)$$

where n denotes the Phong shininess factor and $\vec{R} = 2\vec{G}(\vec{G} \cdot \vec{E}) - \vec{E}$ is the reflect vector. Using the view vector $\vec{E}$ for the light direction ensures that the brightest areas are directly in front of the viewer. It has been found that this approach provides best results. Of course, using the gradient table 12 it is also possible to implement other methods of shading as well as other light sources such as a point light source in order to adapt the visualization to other applications.

A GPU shader program is then used to perform the gradient dependent rendering. The results from evaluating equations (4) and (5) are stored in an 256×256 array. The results of silhouette evaluation are stored as an offset. As discussed above, each voxel in the 3D RGB array 16 has an index into the quantized gradient table 12 stored with the R component being the high order byte and the G component being the low order byte, FIG. 6. This translates directly into (u, v) array coordinates of the display intensity table 20 for the gradient dependent rendering. The gradient magnitude |Δ| is also stored in the same 3D array 16 for the application of other transfer functions. The GPU fragment program then simply performs an array indirection for each voxel to retrieve the silhouette or shading intensity, FIG. 6. The results from the silhouette calculation are stored as an offset such that if the user selects the silhouette function, the GPU shader program simply adds this offset to the u coordinate. This allows a user to select both silhouette enhancements for one material and shading for another.

As described above, when the B-spline subdivision is applied to the ROI 22, the gradients are also subdivided. In order to still be able to use the above silhouette and shading process, an index for each of the new finer gradients into the quantized gradient table 12 is determined. Once the new finer gradients have been determined the same quantization process from lines 1 to 5 of Quantize Gradient is applied to each new finer gradient to determine a value res. However, the display intensity table 20 requires the index at which res is stored and not the actual value res; and the index at which res resides is also inserted into the index table 14 at res, FIG. 5*a*.

In an additional step in the pre-process stage after the quantized gradient table 12 is generated, the index table 14 is completely filled by inserting the closest existing index into each empty slot, FIG. 5*b*. Since the value of res from the gradient quantization process represents the gradient in a packed integer format, the resulting index table 14 is "sorted". Filling the index table 14 with the closest existing indices allows simply applying the quantization process to any arbitrary gradient vector and determining the closest—most similar—existing vector in the quantized gradient table 12 and retrieving the vector's index. FIG. 5*b* illustrates accessing a quantized gradient using indices or arbitrary vectors.

Table 1, shows the results for error and lookup time. The error was calculated by generating a table from a variety of data sets and then indexing 20 million randomly generated gradient vectors and calculating cos(θ) between the random vector and the result returned from the quantized gradient table 12. The timing results are for performing 2 million lookups using the secondary indexing process—a typical size for the ROI 22. The results indicate that minimal error and feedback at interactive rates are possible using this process if an appropriate value for γ in the Quantize Gradient process is chosen.

A rendering pipeline then comprises the following five main steps:
(1) updating the ROI 3D array 16 using B-spline subdivision at each instance the ROI 22 is moved;
(2) updating the array 20 that stores the results of equations (4) and (5) at each instance the viewing direction changes;
(3) rendering the original 3D volumetric dataset 10 as a 3D array;
(4) rendering the ROI 22 as a 3D array; and,
(5) applying the pre-selected transfer functions to the two 3D arrays.

The transfer function used to apply color is a 2D transfer function employing a 2D histogram of intensities and gradient magnitudes. Users are provided with the ability to select an area on the 2D histogram and designate a color. When this is performed, a 2D RGBA array representing the entire area of the 2D histogram is updated by setting the color for texels in the user selected area to the designated color. During rendering the GPU fragment shader program performs an array indirection using the intensity and gradient magnitude of a current voxel as array coordinates to retrieve a color from the 2D RGBA array representing the area of the 2D histogram.

Figure 7:
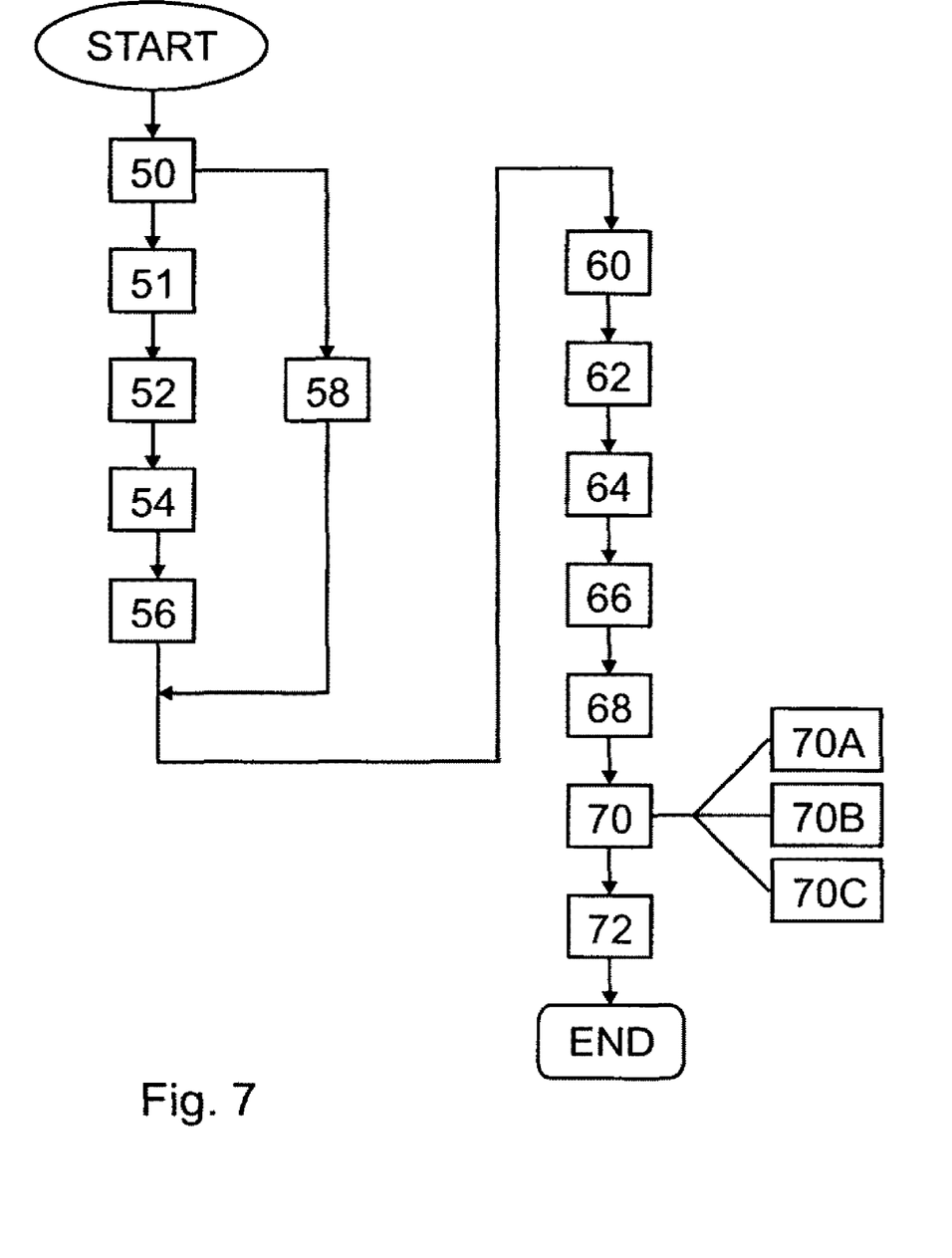
FIG. 7 is a simplified flow diagram illustrating a preferred embodiment of the method for processing a volumetric dataset for providing close-up visualization of a subset therefrom according to the invention.

Referring to FIG. 7, a simplified flow diagram of a preferred embodiment of method for processing a volumetric dataset for providing close-up visualization of a subset therefrom according to the invention is shown. Upon receipt of the volumetric dataset 10 indicative of one of an object and a physical event, a quantized gradient vector is determined for each voxel of the volumetric dataset 10—box 50. Referring to boxes 52 and 54, a gradient table 12 comprising the quantized gradient vectors of the volumetric dataset 10 and a secondary gradient table 14 comprising indices pointing to respective entries in the gradient table 12 are generated, respectively. A 3D array index table 16 comprising an index into the gradient table 12 for each voxel of the volumetric dataset 10 is then generated—box 56. Referring to box 58, low resolution data indicative of a low resolution approximation of the volumetric dataset 10 are determined. These low resolution data are then rendered during user interaction. The determination of the low resolution data is performed either parallel to the processing shown in boxes 51 to 56, or after processing step 56. Optionally, it is performed after a first user interaction. However, this option is not preferred since it causes some delay in the response at the instance of the first interaction. Referring to box 60, subset data indicative of a subset 22 are received. For example, the subset data are received from a user during interaction via a keyboard or a graphical user interface. The subset data are indicative of a location of the subset 22 within the volumetric dataset 10 and of an orientation of the same. Optionally, the subset data are also indicative of size and/or shape of the subset 22, if the processing allows for variable size and/or shape. The subset 22 is then subdivided—box 62- and a quantized new gradient vector is determined for each new voxel of the subdivided subset 22—box 64. Using the secondary gradient table 14, a closest quantized gradient vector of the gradient table 12 and its index is determined for each new quantized gradient vector—box 66. A 3D array subset index table 16 comprising an index into the gradient table 12 for each voxel of the subdivided subset is then generated—box 68. Using the 3D array index table and the 3D array subset index table, the volumetric dataset and the subdivided subset, respectively, are then rendered—box 70—and graphically displayed—box 72. When data indicative of a second subset are received, the processing according to boxes 62 to 72 are repeated for the second subset. The rendering process in box 70 comprises, for example, generating a display intensity table with the display intensity being determined based on an inner product of the quantized gradient vectors of the gradient table with a viewing vector—box 70A, determining display data indicative of a silhouette based on the display intensities of the display intensity table—box 70 B, and repeating the processing of boxes 70A and 70B for other viewing vectors—box 70C if the viewing direction has changed.

Referring to box 72, the rendered volumetric dataset and the rendered volumetric subset are, for example, simultaneously displayed on a graphical display with the rendered volumetric subset being displayed in a predetermined close-up area on the graphical display, as shown in FIGS. 3a and 3b. A visual cue 26 is provided to connect the close-up area 24 with the location of the volumetric subset 22 within the volumetric dataset 10. For example, a user is enabled to rotate the subset illustrated in the close-up area while keeping the viewing direction on the volumetric dataset or, alternatively, the viewing directions of the volumetric dataset and the subset are changed simultaneously. Preferably, the close-up area is of circular or rectangular shape and the visual cue comprises a translucent truncated cone or a translucent truncated pyramid, respectively. Optionally, luminance of the visual cue changes with depth of the location of the volumetric subset within the volumetric dataset in the viewing direction of the volumetric dataset. In its simplest form the visual cue is a line connecting a point on the circumference of the close-up area with the location of the subset. Further optionally, the user is enabled to select at least one of size, shape and location of the close-up area 24. Of course it is also possible to use different rendering techniques for rendering the volumetric dataset and the subset to highlight relevant information. For example, the subset is rendered using maximum intensity projection to isolate and visualize a blood vessel while the volumetric dataset is rendered using surface rendering to help to indicate where the subset is located within the volumetric dataset. Further optionally, the volumetric dataset is rendered such that voxels located in front of the volumetric subset in the viewing direction of the volumetric dataset are displayed in a transparent fashion. This is especially helpful during user interaction for selecting location and orientation of the subset. Optionally, indicators 30 and 32 are generated for graphically indicating the volumetric subset within the volumetric dataset.

Further optionally, graphical data are generated to enable a user to select at least a plane 34 within the volumetric subset. From the data of at least a plane 34 within the volumetric subset are received. Visualization data of the at least a plane are then determined in dependence upon the volumetric subset and, using the graphical display the visualization data of the at least a plane are then displayed in at least a second close-up area 36 on the graphical display.

Figure 8:
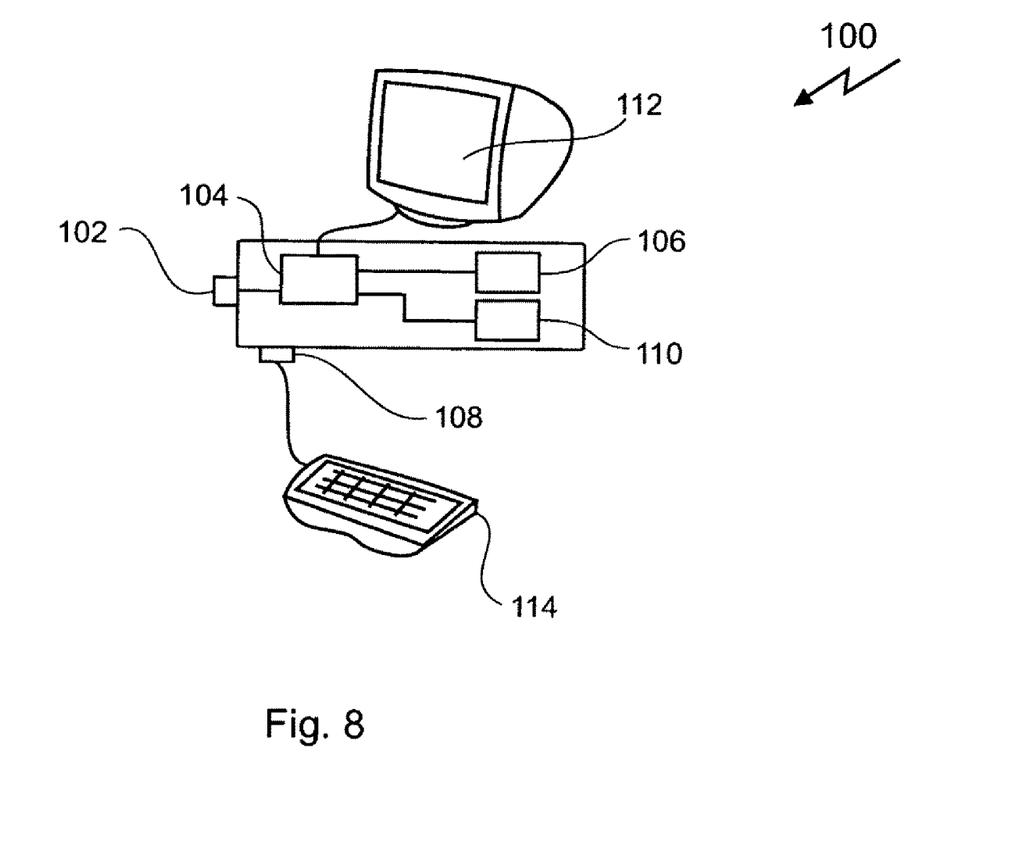
FIG. 8 is a simplified block diagram illustrating a preferred embodiment of a system for processing a volumetric dataset for providing close-up visualization of a subset therefrom according to the invention; and, FIGS. 9*a* and 9*b* are diagrams illustrating contextual close-up images of MRI scans using the method for processing a volumetric dataset for providing close-up visualization of a subset therefrom according to the invention.

Referring to FIG. 8, a signal processing system 100 according to the invention for implementing the above processing methods is shown. Volumetric data are received at input port 102. Using electronic circuitry such as a processor 104 the data are then digitally processed. The system 100 comprises a storage medium 110 having stored therein executable commands for execution on the processor 104 for performing the processing corresponding to the above processing methods. Alternatively, the processor 104 comprises electronic circuitry designed for performing at least a portion of the processing in a hardware implemented fashion. The system 100 further comprises memory 106 such as RAM in communication with the processor 104 for storing at least one of the gradient table 12, the secondary gradient table 14, the 3D array index table 16 and the 3D array subset index table 16. The processing is controlled by a user viewing, for example, a graphical representation of the rendered data and by providing control commands via port 108—connected, for example, to a keyboard 114—to the processor 104. Preferably, the display 112 is a graphical user interface facilitating user interaction during processing.

Figure 9A:
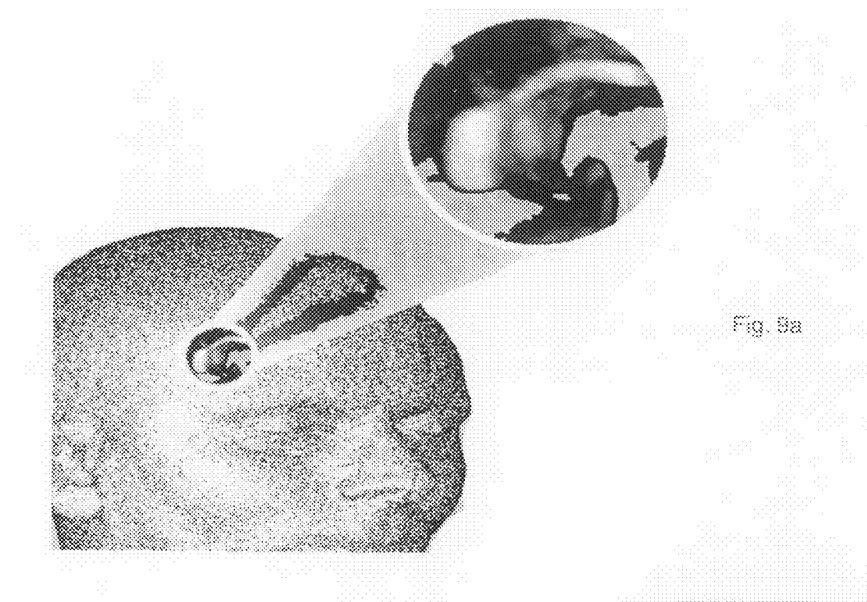
Figure 9B:
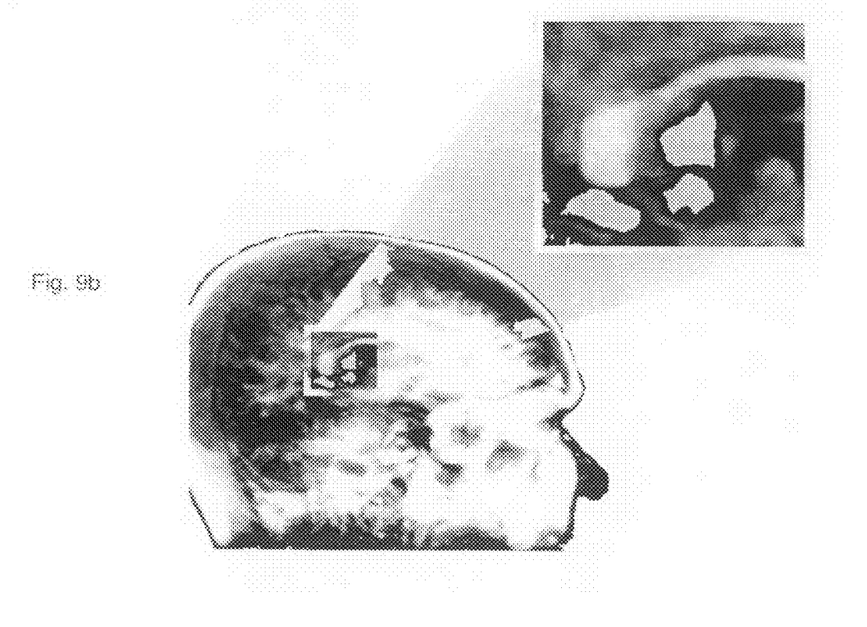

FIGS. 9a and 9b illustrate a contextual close-up of MRI scans of a brain with circular and rectangular close-up areas, respectively. In both images, internal features are shown clear and distinguishable in the close-up areas while the truncated cone and pyramid, respectively, contextualize the enlarged features.

A main issue regarding volumetric gradient dependent rendering is the evaluation of the inner products between the gradient and other directions such as viewing and lighting. The method for processing a volumetric dataset for providing close-up visualization of a subset therefrom according to the invention provides a gradient quantization process that requires minimal generation time, has minimal error, and fast data retrieval. In addition, while rendering the subset, accessing a quantized gradient with an arbitrary normalized vector is fast due to the dual access gradient quantization data structure, i.e. the secondary gradient table. The dual access gradient quantization data structure has a fast pre-processing stage and provides substantially immediate access to a quantized gradient using either an index or an arbitrary normalized vector. Therefore, the above method provides fast computation at interactive rates resulting in clear, enlarged high-resolution images of a ROI and allows a user to freely move and visualize the ROI within the volumetric dataset and with any orientation. Furthermore, the above method is easily implemented using off-the-shelf GPUs on a personal computer or workstation. For example, the images shown in FIGS. 9a and 9b have been generated using an AMD Athlon 2500 with 1.25 GB of RAM and using an OpenGL/ATI radeon 9550 graphics card.

Numerous other embodiments of the invention will be apparent to persons skilled in the art without departing from the spirit and scope of the invention as defined in the appended claims.

What is claimed is:

1. A method for processing a volumetric dataset for providing close-up visualization of a subset therefrom comprising:
    receiving the volumetric dataset, the volumetric dataset being indicative of one of an object and a physical event;
    determining a quantized gradient vector for each voxel of the volumetric dataset;
    generating a gradient table comprising the quantized gradient vectors of the volumetric dataset;
    generating a secondary gradient table comprising indices pointing to respective entries in the gradient table;
    generating a 3D array index table, the 3D array index table comprising an index into the gradient table for each voxel of the volumetric dataset;
    receiving first subset data indicative of a first subset;
    subdividing the first subset;
    determining a quantized new gradient vector for each new voxel of the subdivided first subset;
    using the secondary gradient table determining for each new quantized gradient vector a closest quantized gradient vector of the gradient table and its index;
    generating a 3D array subset index table, the 3D array subset index table comprising an index into the gradient table for each voxel of the subdivided first subset;
    using the 3D array index table and the 3D array subset index table, rendering the volumetric dataset and the subdivided first subset, respectively; and,
    graphically displaying the rendered volumetric dataset and the rendered subdivided first subset.

2. A method for processing a volumetric dataset for providing close-up visualization of a subset therefrom as defined in claim 1 comprising filling empty slots of the secondary gradient table with a closest existing index.

3. A method for processing a volumetric dataset for providing close-up visualization of a subset therefrom as defined in claim 1 wherein the subset is subdivided using a B-spline subdivision process.

4. A method for processing a volumetric dataset for providing close-up visualization of a subset therefrom as defined in claim 3 wherein the quantized new gradient vectors are determined using a B-spline subdivision process.

5. A method for processing a volumetric dataset for providing close-up visualization of a subset therefrom as defined in claim 2 wherein the quantized gradients are determined such that each of the indices pointing into the gradient table is characterized using two bytes.

6. A method for processing a volumetric dataset for providing close-up visualization of a subset therefrom as defined in claim 5 wherein the 3D array index table is generated such that the 3D array index table has a RGB structure with the R component being a high order byte of the index, the G component being a low order byte of the index into the gradient table, and the B component being a gradient magnitude.

7. A method for processing a volumetric dataset for providing close-up visualization of a subset therefrom as defined in claim 1 comprising:
receiving second subset data indicative of a second subset;
subdividing a second subset;
determining a quantized new gradient vector for each new voxel of the subdivided second subset;
using the secondary gradient table determining for each new quantized gradient vector a closest gradient vector of the gradient table and its index;
generating a second 3D array subset index table, the second 3D array subset index table comprising an index into the gradient table for each voxel of the subdivided second subset;
using the second 3D array subset index table, rendering the subdivided second subset; and,
graphically displaying the rendered volumetric dataset and the rendered subdivided second subset.

8. A method for processing a volumetric dataset for providing close-up visualization of a subset therefrom as defined in claim 7 wherein the second subset data are indicative of a second subset placed at a different location within the volumetric dataset than the first subset.

9. A method for processing a volumetric dataset for providing close-up visualization of a subset therefrom as defined in claim 7 wherein the subset data are indicative of a second subset having a different orientation than the first subset.

10. A method for processing a volumetric dataset for providing close-up visualization of a subset therefrom as defined in claim 7 wherein the subset data are indicative of a second subset having a different size than the first subset.

11. A method for processing a volumetric dataset for providing close-up visualization of a subset therefrom as defined in claim 1 comprising generating a display intensity table with the display intensity being determined based on an inner product of the quantized gradient vectors of the gradient table with a viewing vector.

12. A method for processing a volumetric dataset for providing close-up visualization of a subset therefrom as defined in claim 11 comprising determining display data indicative of a silhouette based on the display intensities of the display intensity table.

13. A method for processing a volumetric dataset for providing close-up visualization of a subset therefrom as defined in claim 11 comprising generating a second display intensity table based on a second other viewing vector.

14. A method for processing a volumetric dataset for providing close-up visualization of a subset therefrom as defined in claim 1 comprising determining low resolution data indicative of a low resolution approximation of the volumetric dataset.

15. A method for processing a volumetric dataset for providing close-up visualization of a subset therefrom as defined in claim 14 wherein the low resolution data are determined using a reverse B-spline subdivision process.

16. A method for processing a volumetric dataset for providing close-up visualization of a subset therefrom as defined in claim 14 comprising rendering the low resolution data during user interaction.

17. A method for processing a volumetric dataset for providing close-up visualization of a subset therefrom as defined in claim 1 wherein the rendered volumetric dataset and the rendered subdivided first subset are displayed simultaneously with the rendered volumetric subset being displayed in a predetermined close-up area of a graphical display.

18. A method for processing a volumetric dataset for providing close-up visualization of a subset therefrom as defined in claim 17 comprising providing a visual cue connecting the close-up area with a location of the subset within the volumetric dataset.

19. A non-transitory storage medium having stored therein executable commands for execution on a processor, the processor when executing the commands performing processing a volumetric dataset for providing close-up visualization of a subset therefrom comprising:
receiving the volumetric dataset, the volumetric dataset being indicative of one of an object and a physical event;
determining a quantized gradient vector for each voxel of the volumetric dataset;
generating a gradient table comprising the quantized gradient vectors of the volumetric dataset;
generating a secondary gradient table comprising indices pointing to respective entries in the gradient table;
generating a 3D array index table, the 3D array index table comprising an index into the gradient table for each voxel of the volumetric dataset;
receiving first subset data indicative of a first subset;
subdividing the first subset;
determining a quantized new gradient vector for each new voxel of the subdivided first subset;
using the secondary gradient table determining for each new quantized gradient vector a closest quantized gradient vector of the gradient table and its index;
generating a 3D array subset index table, the 3D array subset index table comprising an index into the gradient table for each voxel of the subdivided first subset;
using the 3D array index table and the 3D array subset index table, rendering the volumetric dataset and the subdivided first subset, respectively; and,
graphically displaying the rendered volumetric dataset and the rendered subdivided first subset.

20. A non-transitory storage medium as defined in claim 19 having stored therein executable commands for execution on a processor, the processor when executing the commands performing:
receiving second subset data indicative of a second subset;
subdividing a second subset;
determining a quantized new gradient vector for each new voxel of the subdivided second subset;
using the secondary gradient table determining for each new quantized gradient vector a closest gradient vector of the gradient table and its index;
generating a second 3D array subset index table, the second 3D array subset index table comprising an index into the gradient table for each voxel of the subdivided second subset;
using the second 3D array subset index table, rendering the subdivided second subset; and, graphically displaying the rendered volumetric dataset and the rendered subdivided second subset.

21. A non-transitory storage medium as defined in claim 19 having stored therein executable commands for execution on a processor, the processor when executing the commands performing:
  determining low resolution data indicative of a low resolution approximation of the volumetric dataset.

22. A non-transitory storage medium as defined in claim 21 having stored therein executable commands for execution on a processor, the processor when executing the commands performing:
  rendering the low resolution data during user interaction.

23. A system for processing a volumetric dataset for providing close-up visualization of a subset therefrom comprising:
  a first input port for receiving the volumetric dataset, the volumetric dataset being indicative of one of an object and a physical event;
  a processor in communication with the first and the second input port for processing the volumetric dataset comprising:
    determining a quantized gradient vector for each voxel of the volumetric dataset;
    generating a gradient table comprising the quantized gradient vectors of the volumetric dataset;
    generating a secondary gradient table comprising indices pointing to respective entries in the gradient table;
    generating a 3D array index table, the 3D array index table comprising an index into the gradient table for each voxel of the volumetric dataset;
    receiving subset data indicative of a subset;
    subdividing the subset;
    determining a quantized new gradient vector for each new voxel of the subdivided subset;
    using the secondary gradient table determining for each new quantized gradient vector a closest quantized gradient vector of the gradient table and its index;
    generating a 3D array subset index table, the 3D array subset index table comprising an index into the gradient table for each voxel of the subdivided subset; and,
    using the 3D array index table and the 3D array subset index table, rendering the volumetric dataset and the subdivided subset, respectively, and providing data in dependence thereupon; and,
  an output port in communication with the processor for providing the data indicative of the rendered volumetric dataset and the rendered subdivided subset.

24. A system for processing a volumetric dataset for providing close-up visualization of a subset therefrom as defined in claim 23 comprising memory in communication with the processor for storing at least one of the gradient table, the secondary gradient table, the 3D array index table and the 3D array subset index table.

25. A system for processing a volumetric dataset for providing close-up visualization of a subset therefrom as defined in claim 24 comprising a storage medium in communication with the processor having stored therein executable commands for execution on the processor, the processor when executing the commands performing at least a portion of the processing of the volumetric dataset.

26. A system for processing a volumetric dataset for providing close-up visualization of a subset therefrom as defined in claim 24 wherein the processor comprises electronic circuitry designed for performing at least a portion of the processing of the volumetric dataset.

27. A system for processing a volumetric dataset for providing close-up visualization of a subset therefrom as defined in claim 24 comprising a control port in communication with the processor for receiving control commands for controlling at least a portion of the processing of the volumetric dataset.

28. A system for processing a volumetric dataset for providing close-up visualization of a subset therefrom as defined in claim 27 comprising a graphical display in communication with the processor for displaying the data indicative of the rendered volumetric dataset and the rendered subdivided subset in a graphical fashion.

29. A system for processing a volumetric dataset for providing close-up visualization of a subset therefrom as defined in claim 28 wherein the graphical display comprises a graphical user interface.

* * * * *